United States Patent
Antoni et al.

(10) Patent No.: US 10,101,349 B2
(45) Date of Patent: Oct. 16, 2018

(54) ANALYTICAL TEST MANAGEMENT SYSTEM AND METHOD

(71) Applicant: Roche Diagnostics Operations, Inc., Indianapolis, IN (US)

(72) Inventors: Sascha Martin Antoni, Penzberg (DE); Martin Burri, Bettwil (CH); Werner Doeppen, Eberfing (DE); Bernhard Eckert, Weilheim (DE); Elke Faatz, Huglfing (DE); Barbara Upmeier, Iffeldorf (DE); Andreas Woeste, Munich (DE); Dieter Roessler, Kirchseeon (DE); Elena Pfaffenrot, Eich (CH)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 234 days.

(21) Appl. No.: 15/249,834

(22) Filed: Aug. 29, 2016

(65) Prior Publication Data

US 2017/0067922 A1    Mar. 9, 2017

(30) Foreign Application Priority Data

Sep. 4, 2015  (EP) .................................... 15183878

(51) Int. Cl.
  *G01N 35/00*   (2006.01)
  *G01N 35/10*   (2006.01)
  *G05B 19/042*  (2006.01)

(52) U.S. Cl.
  CPC ... *G01N 35/0092* (2013.01); *G01N 35/00613* (2013.01); *G01N 35/00712* (2013.01);
  (Continued)

(58) Field of Classification Search
  CPC ....... G01N 35/00584; G01N 35/00871; G01N 35/0092; G01N 35/0095;
  (Continued)

(56) References Cited

U.S. PATENT DOCUMENTS 6,225,067 B1    5/2001  Rogers
2007/0196909 A1*  8/2007  Showalter .............. G06Q 10/00
                                              435/283.1

(Continued)

FOREIGN PATENT DOCUMENTS

EP      2450711 A1    1/2013
WO   1994/011838 A1    5/1994

*Primary Examiner* — Christopher Adam Hixson
(74) *Attorney, Agent, or Firm* — Roche Diagnostics Operations, Inc.

(57) ABSTRACT

A test management system is presented. The system comprises an analyzer to perform tests a sample according to a first set of instructions, a manager module connected to the analyzer, and a first order interface connected to the manager module. The manager module directs activity of the analyzer according to a second set of instructions. The first order interface receives an order for a first analytical test and a second analytical test and transmits the order to the manager module. If the order is for the first analytical test, the test manager module forwards the order directly to the analyzer and the sample is analyzed by the analyzer according to the first set of instructions. If the order is for the second analytical test, the manager module handles the order according to the second set of instructions and generates and transmits secondary test requests to the analyzer.

16 Claims, 9 Drawing Sheets

(52) U.S. Cl.
CPC ... *G01N 35/00871* (2013.01); *G01N 35/1072* (2013.01); *G05B 19/042* (2013.01); *G01N 35/0095* (2013.01); *G01N 2035/0091* (2013.01); *G01N 2035/00326* (2013.01); *G01N 2035/00881* (2013.01); *G01N 2035/1032* (2013.01); *G05B 2219/32258* (2013.01); *Y02P 90/20* (2015.11)

(58) Field of Classification Search
CPC ........ G01N 2035/00881; G05B 19/042; G05B 2219/32258
See application file for complete search history.

(56) References Cited

U.S. PATENT DOCUMENTS

| | | | | |
|---|---|---|---|---|
| 2011/0022327 | A1* | 1/2011 | Busenhart | G16H 40/63 702/19 |
| 2012/0275885 | A1* | 11/2012 | Furrer | G01N 35/00732 414/222.02 |

\* cited by examiner

ANALYTICAL TEST MANAGEMENT SYSTEM AND METHOD

CROSS-REFERENCE TO RELATED APPLICATIONS

This application claims priority to EP 15183878.6, filed Sep. 4, 2015, which is hereby incorporated by reference.

BACKGROUND

The present disclosure generally relates to a system and method for managing analytical tests and, in particular, to a system and method for managing analytical tests for managing complex combinations of analytical tests.

In certain circumstances, medically important information does not come from a single test, but rather, it is a combination of tests that yields the result needed by a health care professional to make a treatment decision for a patient. As the complexity of these combinations of tests increases, the likelihood that a mistake is made increases, particularly when the tests are ordered individually and results of differing quality are combined to provide the result on which treatment is based.

A related challenge facing providers of medical testing systems is that along with increased need to extract additional medical value from existing and new combinations of tests come increased regulatory and quality requirements. The regulatory demand placed on these providers is particularly heightened when the outcome of a complex set of tests is the basis of an impactful diagnosis, or a decision regarding the choice of drug to most effectively combat a potentially fatal disease.

Current medical testing systems, particularly when housed in a certified laboratory and staffed by highly qualified personnel, can often meet the regulatory and associated quality control demands that accompany high medical value testing. However, the same is not always true in hospital laboratories, particularly small hospital laboratories, where staffing shortages and lack of training can make it necessary for samples to be transferred to a certified laboratory. Transfer of samples can unnecessarily delay time-critical treatment decisions and often reduces the time during which valid test results can be obtained because samples can degrade over time. And, even in certified laboratories, there are pressures to increase throughput, lower personnel costs, and reduce waste and mistakes, as well as to provide a widening array of test offerings to their customers.

Therefore, there is a need for a system and method for managing the testing of biological samples that can help meet the demands of patients and health-care providers, now and in the future, in a reliable and controllable manner.

SUMMARY

According to the present disclosure, an analytical test management system is disclosed. In this embodiment, the system can include an analyzer configured to perform an analytical test on a biological sample, where the test can be conducted according to a first set of instructions that can be stored in an analyzer memory. For example, the analyzer can follow the first set of instructions to perform physical and/or chemical interrogations and manipulations that can lead to a test result. The system can also include a test manager module that can be communicatively connected to the analyzer and that can use a second set of instructions stored in a test manager module memory to direct the activity of the analyzer. A test order interface communicatively connected to the test manager module can further be included and can be configured to receive a test order for one of an analytical test of a first type (for example, a simple, single analyte test) and an analytical test of a second type (for example, a workflow of several possible tests). The interface can transmit the test order to the test manager module and, if the test order is for the analytical test of the first type, the test manager module can be configured to forward the test order directly to the analyzer and the biological sample can be analyzed by the analyzer according to the first set of instructions. If, however, the test order is for the analytical test of the second type, for example, a combination of tests, the test manager module can be configured to handle the test request according to the second set of instructions and to generate and transmit one or more secondary test requests to the analyzer for execution, at one or more various times.

In accordance with one embodiment of the present disclosure, the analyzer memory can include a first set of instructions of a first type and a first set of instructions of a second type. The first set of instructions of the first type can be used by the analyzer to process the test order for the analytical test of the first type and the first set of instructions of the second type can be used by the analyzer to process the test order for the analytical test of the second type according to the one or more secondary test requests. For example, the first set of instructions of the first type can be a set of instructions that can be used to carry out a simple test that can directly provide an analysis result, whereas the first set of instructions of the second type can be a set of instructions that can provide an intermediate result that can perhaps be further used by the test manager module to generate additional secondary tests requests according to the second set of instructions.

In accordance with another embodiment of the present disclosure, a method for managing analytical tests is disclosed. The disclosed method can include storing a first set of instructions in a memory of an analyzer configured to perform an analytical test on a biological sample and storing a second set of instructions in a memory of a test manager module. A test order of one of two types can be received at the test manager module through a first test order interface and the test manager can determine the test order type. If the test order is determined to be for the analytical test of the first type, the test order can be sent directly to the analyzer to analyze the biological sample according to the first set of instructions. If the test order is determined to be for the analytical test of the second type, the test manager module can generate, according to the second set of instructions, one or more secondary test requests and these one or more secondary test requests can be transmitted to the analyzer.

In accordance with yet another embodiment of the present disclosure, the method can further include storing in the analyzer memory a first set of instructions of a first type and a first set of instructions of a second type and analyzing the biological sample according to the first set of instruction of the first type if the test order is for the analytical test is of the first type, and analyzing the biological sample according to the first set of instructions of the second type in response to the one or more secondary test requests if the test order is for the analytical test is of the second type.

Accordingly, it is a feature of the embodiments of the present disclosure to provide a system and method for managing analytical tests, particularly, for managing complex combinations of analytical tests, in a reliable and controllable manner. Other features of the embodiments of the present disclosure will be apparent in light of the description of the disclosure embodied herein.

BRIEF DESCRIPTION OF THE SEVERAL VIEWS OF THE DRAWINGS

The following detailed description of specific embodiments of the present disclosure can be best understood when read in conjunction with the following drawings, where like structure is indicated with like reference numerals and in which.

DETAILED DESCRIPTION

Figure 1:
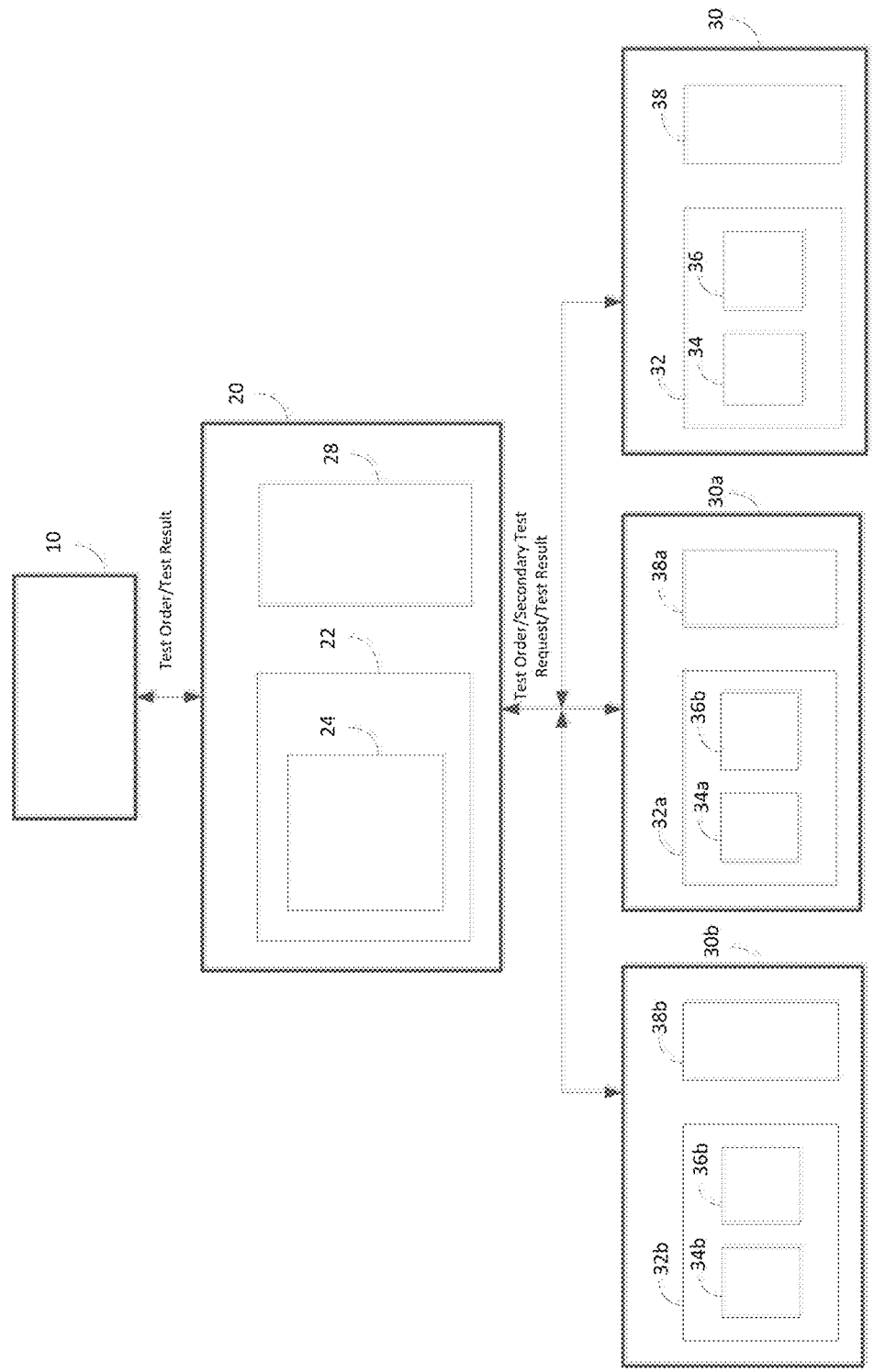
FIG. 1 illustrates analytical test management system according to an embodiment of the present disclosure.

In the following detailed description of the embodiments, reference is made to the accompanying drawings that form a part hereof, and in which are shown by way of illustration, and not by way of limitation, specific embodiments in which the disclosure may be practiced. It is to be understood that other embodiments may be utilized and that logical, mechanical and electrical changes may be made without departing from the spirit and scope of the present disclosure.

As used herein, "a" and "the" can refer to both the singular and plural referents unless clearly indicated otherwise. The following examples are provided solely to assist the reader in understanding the invention as defined in the claims that follow.

An analytical test management system is disclosed that can include an analyzer, a test manager module, and a first test order interface. The analyzer can be configured to perform an analytical test on a biological sample according to a first set of instructions. The instructions for performing the analytical test can be stored in an analyzer memory. The test manager module can be communicatively connected to the analyzer and can be configured to direct activity of the analyzer according to a second set of instructions, which instructions are stored in a test manager module memory. The first test order interface, which can be communicatively connected to the test manager module, can be configured to receive a test order for one of an analytical test of a first type and an analytical test of a second type and to transmit the test order to the test manager module. The test manager module can be configured to forward the test order directly to the analyzer if the test order is for the analytical test of the first type and the biological sample can be analyzed by the analyzer according to the first set of instructions. If, however, the test order is for the analytical test of the second type, the test manager module can be configured to handle the test order according the second set of instructions and to generate and transmit one or more secondary test requests to the analyzer.

The biological sample to be analyzed can be received by an analyzer in native form or received in a pre-treated form, for example, after being transported from a separate pre-analytical system or device. Alternatively, or in addition, the analyzer itself can also perform one or more pre-treatment procedures prior to analysis of the biological sample. Examples of pre-treatment procedures can include preparation of aliquots, separation of sample components, concentration or dilution of the sample or components thereof, and removal of interfering substances or materials. Examples of biological samples can include blood, saliva, ocular lens fluid, cerebrospinal fluid, sweat, urine, stool, semen, milk, ascites fluid, mucous, synovial fluid, pus, peritoneal fluid, amniotic fluid, tissue, and cultured cells, or any sample obtained or otherwise derived from the same, for example, serum obtained from blood.

As shown in the embodiment of FIG. 1, a first test order interface 10 can be communicatively connected to the test order manager module 20. The first test order interface 10 that is communicatively connected to the test manager module can be, for example, a laboratory system control device, such as a PC system that can be used by laboratory personnel to enter test orders for execution on one of several analyzers and to receive test results through the test order manager module 20. Alternatively, the first test order interface 10 can receive test orders that can be entered into a laboratory middleware system, that can be communicated through a laboratory middleware system from a host system (e.g. an HIS or LIS system), or that can be communicated directly from a host system. Likewise, test results can be delivered back to the middleware system (for example, for QC checks) and to the host system (for example, for viewing by a healthcare professional). For example, the first test order interface can receive test orders from any one of several host system user interfaces that are communicatively connected to the host system, such as host system interfaces that are distributed within a health care facility, and deliver test results back to those host system user interfaces. It can be possible and typical to have one or more user interfaces for entry of test order through each of the laboratory system control device, the middleware system, and the host system.

As further shown in the embodiment of FIG. 1, the test order manager module 20 can be communicatively connected to an analyzer 30 and can be further communicatively connected to one or more additional analyzers 30a, 30b. The analyzer 30 and additional analyzer(s) 30a, 30b can be of any type of known or yet to be developed system that can interrogate a biological sample using physical, chemical and/or biological methods to provide a test result for a particular analyte or group of analytes. The test result can be, for example, raw data or counts, a calculated result, or a combination thereof. The analyzer can utilize any of a variety of techniques and methods to provide a measure of an analyte's presence, and/or concentration, and/or interaction with other molecules or cells within the biological sample. Examples of analyzers can include immunochemical analyzers, mass spectrometric analyzers, cytometric analyzers, chemical analyzers, fluorescence analyzers, electrochemical analyzers, electro-physical analyzers, optical analyzers, microscopic analyzers, nucleic acid sequence analyzers, PCR (or other NA amplification) analyzers, and combinations thereof.

The analyzer 30 and the one or more additional analyzers 30a, 30b can include both software and hardware components that can be used together to receive a sample, receive a test order or test request associated with the sample, analyze or otherwise process the sample according to the test order or test request, and can provide a test result as output. The analyzer 30 and the one or more additional analyzers 30a, 30b can include an analyzer controller 38, 38a, 38b; which also can be referred to as an analyzer CPU or an analyzer processor configured to direct the handling of test orders, secondary test requests and test results and can direct the performance of manipulations and measurements made on a sample. The logic used by the controller to operate an analyzer 30 and the one or more additional analyzers 30a, 30b can be embodied in software, firmware, or a combination of both. The hardware components that can be part of an analyzer 30 and the one or more additional analyzers 30a, 30b can include, for example, pipettors; barcode readers; RFID readers; NFC readers; grippers, tube handlers, rack handlers, reagent pack handlers and other structures to move samples and consumables around inside an analyzer; waste handlers; mixers; shakers; stirrers; incubators; heaters; coolers; blood smear generators; sample printing/deposition devices; slide handlers; microscopes; ECL detectors; electrodes; mass detectors; spectrometers; photometers; and the like; and any combination of these and other known or later developed analyzer hardware components.

Also as shown in the embodiment of FIG. 1, the test manager module can include a test manager module memory 22 having stored thereon a second set of instructions 24 for handling an analytical test of the second type. When a test order is received from the first test order interface 10, the test manager module controller 28 can be configured to handle the incoming test order by determining whether the test order is a test order for an analytical test of the first type or is a test order for an analytical test of the second type. If the test order is for an analytical test of the first type, the test manager module controller 28 can forward the test order directly to the analyzer 30 or to one of the additional analyzers 30a, 30b, if they are present, according, for example, to a load balancing algorithm can also be stored in the test manager module memory 22 or according to instructions received from a laboratory middleware system. If the test order is for an analytical test of the second type, the test manager module controller 28 can generate one or more secondary test requests according to the second set of instructions 24, and the one or more secondary test requests can be sent by the test manager module controller 28 to the analyzer 30 or to one of the additional analyzers 30a, 30b, if they are present, according, for example, to a load balancing algorithm also stored in the test manager module memory 22, or according to instructions received from a laboratory middleware system. A test result for an analytical test of the first type can be transmitted from the analyzer 30 or one of the additional analyzers 30a, 30b, received by the test manager module 20, and can passed directly on to the first test order interface 10 for retrieval by a laboratory system control device, a middleware system, and/or a host system. A test result for an analytical test of the second type, in contrast, can be handled further upon receipt in the test manager module 20 according to the second set of instructions and perhaps also in dependence on the test result value.

In certain embodiments, the second set of instructions can also include predefined calculations based on received test results and predefined calculations of quality control measurements received from an analyzer. Calculations can be based on any combination of any number of previously measured test results transmitted from an analyzer to the test manager module and/or qualitative, semi-quantitative and/or quantitative results previously generated in the test manager module according to the second set of instructions.

The second set of instructions can, in other embodiments, define, for example, the order that different analytical tests can be processed in parallel or sequentially on an analyzer, and in still others, define the order in which reagents can be pipetted for tests processed in parallel or sequentially on the analyzer. The second set of instructions can, in some embodiments, include a series of secondary test requests having different dilution factors for automatic repeats to create a valid test result within a predefined measuring range. Alternatively, the second set of instructions can ensure that test that should be done together, and in a particular order, are performed close in time, with the same reagents, and on the same analyzer. In some embodiments, qualitative results can be generated according to the second set of instructions and used to control further processing of a sample. In still other embodiments, the second set of instructions can include one or more decision steps, for example, a comparison of a test result received from an analyzer with a single value to generate a TRUE/FALSE condition. Alternatively, or in addition, the second set of instructions can include one or more decision steps where different values define the next sequence steps, for example, as reflected in additional secondary test request(s), which in turn can lead to additional decisions and/or additional secondary test request(s) and additional calculations before a final analytical test result is provided to a user of the disclosed system. In these ways, and others, complex testing schemes that are not within the capabilities of certain users can be established on a system.

In some embodiments, the one or more secondary test requests can be generated by the test manager module and can be transmitted to the analyzer include at least two secondary test requests. The results from the at least two secondary test requests can be used by the test manager module to determine an analytical result for the analytical test of the second type. In other embodiments, the one or more secondary test requests can be generated by the test manager module and can be transmitted to the analyzer can comprise at least a first secondary test request that can be used by the analyzer to generate a first secondary test result that can be transmitted back to the test manager module, and in some more embodiments, the test manager module can be configured according to the second set of instructions to determine based on the first secondary test result whether one or more additional secondary test requests may be required, and if the one or more additional secondary test requests are required, to generate and transmit the one or more additional secondary test requests to the analyzer. In still more embodiments, combinations of multiple secondary requests can be generated by the test manager module based on multiple results received back from the analyzer in order to automate workflows that might lead to a higher probability of mistakes if done manually by laboratory personnel, and in particular also to ensure that associated QC results can be obtained as needed to ensure that they remain valid for each step of a series of interdependent secondary tests requests and thus that any QC calculations based on those QC results are also valid. Likewise, in order to ensure valid results, the test manager module can respond to test failures at any point in a combination of interdependent secondary test requests in a predetermined manner that ensures reliable results. A further benefit of controlling a test order for an analytical test of the second type through the test manager module is that where a result of a first or some subsequent secondary test request can indicate that no further testing is required, reagents can be saved automatically as the result of the analytical test of the second type can then be provided by the test manager module without unnecessary tests being performed.

In other embodiments, the second set of instructions can be under the control of the vendor of the tests and cannot be altered by an end user. In these embodiments, there can also be the possibility for a vendor to provide testing combinations that meet regulatory requirements for tests used to provide impactful diagnoses (for example, a diagnosis of HIV positive) or determine a course of treatment (for example, Herceptin treatment for an individual with Her2 positive cancer cells present). Vendor reputation can also be safeguarded through vendor control of complex testing procedures.

FIG. 1 also illustrates an embodiment where the analyzer memory 32, 32a, 32b can further include a first set of instructions of a first type 34, 34a, 34b and a first set of instructions of a second type 36, 36a, 36b. The first set of instructions of the first type can be used by the analyzer to process the test order for the analytical test of the first type, whereas the first set of instructions of the second type can be used by the analyzer to process the test order for the analytical test of the second type according to the one or more secondary test requests that can be supplied to the analyzer 30, 30a, 30b by the test manager module 20. For example, the first set of instructions of the first type can be used by the analyzer to process an order for a single analytical result and the first set instructions of the second type can be used by the analyzer to perform a test controlled by the test manager module according to the second set of instructions 24, which may include a combination of multiple test results provided in response to secondary test requests.

In even more embodiments, the first instructions of the first type and the first instructions of the second type can lead to the same set of analytical steps being performed by the analyzer, but in the case of the first instructions of the second type, those instructions can be linked to one or more additional first instructions of the second type, for example, through the second set of instructions according to which the test manager module can direct the analyzer. In other embodiments, the presence of first instructions of the second type 36, 36a, 36b in an analyzer memory 32, 32a, 32b can cause an analyzer processor 38, 38a, 38b to reserve or otherwise link reagents present on the analyzer in order that all reagents necessary to fulfill a test order for an analytical test of the second type performed according to the second set of instructions stored in the test manager module 20. In other more embodiments, the linking of reagents can be performed at the time when the reagents are loaded into an analyzer.

In still other embodiments, the presence of first instructions of the second type in an analyzer memory can cause the analyzer to communicate with the test manager module to determine which reagents may be needed to perform an analytical test of the second type, and then the analyzer processor can link the reagents in the analyzer. In more additional embodiments, the test manager module can instruct the analyzer processor to link reagents in the analyzer only if there are test orders for the analytical test of the second type in a queue of test orders (such as present in the test manager module, a middleware system or host system) that are to be processed by the test manager module. So, for example, there may be certain times of the day in a hospital when orders for analytical tests of the second type arrive in the laboratory and, thus, outside of those times, it may be desirable not to link reagents, since in further more embodiments, when reagents are linked in an analyzer, they can only be used together and when one is depleted or otherwise rendered unusable (for example, through expiration or detected degradation) all linked reagents can be disabled and can be removed. Thus, when it is not necessary to link reagents due to having a test order queue that may contain enough test orders for analytical test orders of the first type to exhaust the reagents present on an analyzer, waste of reagents that may occur upon linking can be avoided.

In other embodiments, reagents that are linked, such as a first reagent and a second reagent, can be utilized according to the second set of instructions stored in the test manager module in a predetermined order. For example, if an analytical test result obtained using either one of the first reagent and the second reagent is in error, a repeat analytical test can be automatically ordered by the test manager module and the first reagent and the second reagent can be again utilized according to the second set of instructions in the same predetermined order to generate a repeat analytical test result.

Since it can be possible for both test orders for an analytical test of the first type and an analytical test of the second type to be in a queue of test orders, and that both types of test are being performed in parallel, in certain embodiments, a quality control result obtained by the analyzer according to the first set of instructions of the first type can be transmitted to and used by the test manager module also as a quality control result for an analytical result according to the first set of instructions of the second type. Once transmitted to the test manager module, the test manager module can use the "copied" quality control result for QC calculations directly, or in a QC calculation that involves combining multiple QC results according to a particular formula. This may be the case where a particular analytical test can be used both to obtain a single result and a result of one of at least two secondary test requests generated in the test manager module and transmitted to the analyzer for execution. An advantage here can be that separate QC runs may not be needed for both types of analytical tests and QC reagents are thus conserved whenever possible.

In still further embodiments, a biological sample can be kept on an analyzer and tested (and possibly re-tested) until the analytical test of the second type is completed according to the second set of instructions stored in the test manager module. Keeping the sample on the analyzer can help ensure that the proper QC can be done on the sample and that consistent results can be obtained, since in such embodiments, the same reagents can be utilized, and those reagents can, for example, be reagents that can be provided in matched sets by a vendor.

Figure 2:
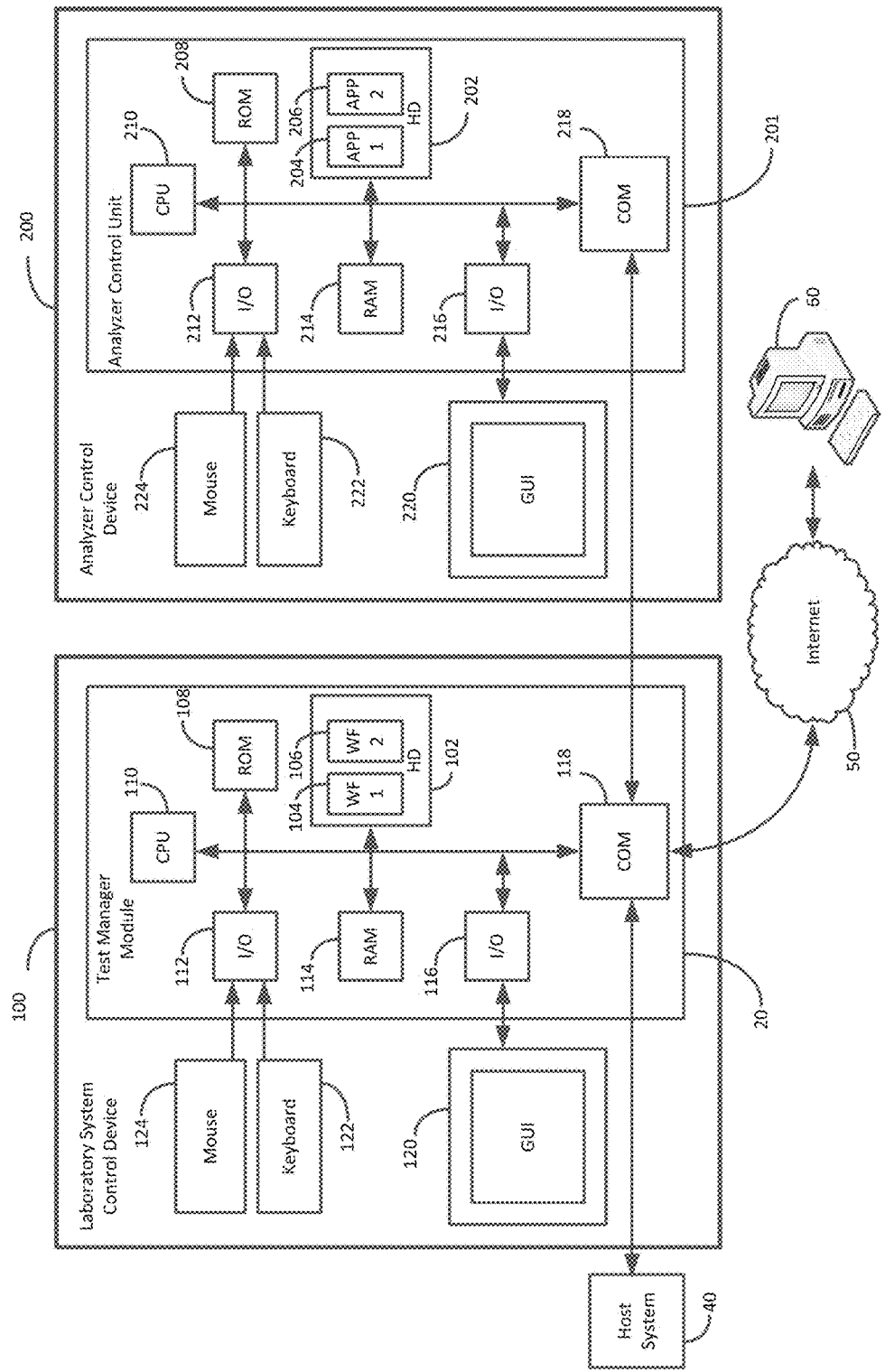
FIG. 2 illustrates analytical test management system according to another embodiment of the present disclosure.

FIG. 2 shows another embodiment of the disclosed system. In this embodiment, the test manager module 20 is shown as a component of a laboratory system control device 100, which can be in control of one or more analyzers through their associated analyzer control device 200, and possibly in control of additional components of a laboratory system, for example one or more pre-analytic devices (such as an aliquoter or a centrifuge) and/or one or more post-analytical devices (such as a refrigerated sample storage and retrieval system). The laboratory system control device 100 can include, for example, a laboratory system user interface 120, a laboratory system keyboard 122 and a laboratory system mouse 124 that are communicatively connected to the test manager module 20 and can be used to input a test order into the system. As such the laboratory system control device can act as the first test order interface 10 of the disclosed system.

Also as shown in FIG. 2, the analyzer control device 200 can also include an analyzer user interface 220, analyzer keyboard 222 and analyzer mouse 224 that can be used to control the analyzer directly, and not through a test manager module, and these human/machine interfaces can be used, for example, to input a test order for execution on an analyzer. In more embodiments, the analyzer control device 200 can be configured only to accept a test order for an analytical test of the first type and not a test order for an analytical test of the second type, and features used to input test orders for an analytical test of the second type can either hidden, not present, or otherwise be masked (such as by non-functional display components, perhaps displayed in blurred or in different colors from other display components) in the analyzer user interface 220.

In more embodiments, one or the other of, or both of, the laboratory system user interface 120 and the analyzer user interface 220 can be touch-screen interfaces and the mouse and keyboard (or other human/machine interfaces, known or yet to be developed) may or may not be present.

Also shown in FIG. 2, is a host system 40 which can also include devices to input test orders that can then be transmitted to the test manager module 20 for processing. As mentioned above, the host system can also include one or more host system human/machine interfaces (not shown) which can be used to input a test order. In some embodiments, a test order for an analytical test of the second type can only be entered through the host system 40. In other embodiments, a test order for an analytical test of the second type can only be entered through the host system 40 or through the laboratory system control device 100, but cannot be entered through analyzer control device 200. In certain embodiments, any of the host system 40; and its associated human/machine interfaces), the laboratory system control device 100, and the analyzer control device 200 can be used to input a test order for an analytical test of the first type.

In even more particular embodiments, the analyzer control device 200 can be configured to only accept test orders for an analytical test of the first type from one class of users (such as healthcare providers), but can be used to accept test orders for an analytical test of the second type from a second class of users holding particular administrative rights (e.g. a service technician, or laboratory manager).

As further illustrated in FIG. 2, the test manager module can include some, all of, or at least the components shown therein. For example, a test manager module can include a test manager module hard drive 102 having stored thereon one or more second sets of instructions 104, 106 that can be used by the test manager module 20 to process a test request for an analytical test of the second type. Additional components of the test manager module 20 can include a ROM 108, a CPU 110, one or more input/output interfaces 112, 116 used to mediate communication between the test manger module 20 and a human/machine interface, such as keyboard 122. Also shown is a RAM 114 which can be used to temporarily store one or more second sets of instructions 104, 106 as they are executed by CPU 110. Test manager module communications interface 118 can function to mediate the transmission of test orders, secondary test requests and test results between the various components and devices, including the host system 40, the laboratory system control device 100 and the analyzer control device 200. In addition, in certain embodiments, the test manager module communications interface 118 can be communicatively connected through an internet 50 to a remote computer 60, which can be a vendor-controlled computer system.

As shown in FIG. 2, an analyzer control unit 201 can include an analyzer control unit hard drive 202 having stored thereon one or more first sets of instructions of a first type 204 and one or more first sets of instructions of a second type 206 that can be used by the analyzer control unit 201 to process, respectively, a test request for an analytical test of the first type and a test request for an analytical test of the second type according to one or more secondary test requests transmitted to the analyzer control unit 201 by the test manager module 20 according to the second set of instructions 104, 106. Additional components of the analyzer control unit 201 can include a ROM 208, a CPU 210, one or more input/output interfaces 212, 116 used to mediate communication between the analyzer control unit 201 and a human/machine interface, such as keyboard 222. Also shown is a RAM 214 which can be used to temporarily store one or more of the first instructions of the first type 204 and one or more of the first instructions of the second type 206 as they are executed by CPU 210. Analyzer communications interface 218 can function to mediate the transmission of test orders, secondary test requests and test results between the test manager module 20 and analyzer control unit 201.

A sequence of processing different assays in multiple steps depending on measured results of previous assays is often described by a vendor of the assays. All the steps have to be done manually or they have to be configured on an analyzer by the customer. In this situation, the final processing sequence of multiple assays is not in the control of the vendor of the assays and can be changed or misused by customer. Depending on the analyzer, not all sequences can be done in a fully automated manner and manual steps may be required to initiate further processing.

Thus, according to one embodiment of the disclosed system and method, a vendor of assays can fully control the sequences of these assays (incl. calculations) and can take responsibility for the final result. Since all steps of such a processing sequence can be done in a fully automated manner without any interaction of a user, there can be a reduction in the possible sources of errors and the processing time can be optimized to a minimum duration.

In some embodiments, one or more second sets of instructions 104, 106 and/or one or more first sets of instructions of a first type 204 and/or one or more first sets of instructions 206 can be transmitted from remote computer 60, which can be a computer under the control of a vendor, for storage in test module hard drive 102 and/or analyzer hard drive 202. Alternatively, first and second sets of instructions can be stored in test module hard drive 102 and/or analyzer hard drive 202 by a vendor-employed service technician after transfer from any known or yet to be developed portable storage medium (for example, a CD or a USB stick). In either case, vendor control of the loading of instructions stored in the test module hard drive 102 and/or analyzer hard drive 202 can decrease the possibility that they may be altered by a user and can help the vendor establish that test available to the user are safe and effective. For example, the vendor can provide a closed system including a test order manager module and prevent user access thereto, such as by keeping some or all of the second set of instructions used by the test manager module hidden from and unalterable by a user.

In other embodiments, the disclosed system can includes a graphical user interface (GUI), which can be any or all of a host system GUI, a laboratory system GUI, an analyzer system GUI or other communicatively connected GUI. The GUI can be configured to display to a user a final result that can be determined based on one or more secondary test results received from the analyzer following execution of the one or more secondary test requests by the analyzer, but not display the one or more secondary test results that were used to determine the final result. An advantage of hiding the underlying secondary test results can be that in some instances, the underlying test results can be misleading, and in other instances, such underlying information may simply not be needed to make a health care decision. The GUI can be further configured to display underlying test details if desired (such as through a drill-down operation), and in some embodiments, such underlying test details can be made visible only to certain users having the appropriate access rights, for example, to a service technician for trouble-shooting purposes. In other embodiments, the results of underlying secondary test results may not be visible on the GUI, but can be provided to a user when a test result report is printed.

Although suggestive of hardwire connections in FIGS. 1 and 2, any or all of the illustrated connections between components can be hardwired or wireless (for example, RF or IR). Communication between system components can be mediated using any known or yet to be developed communications protocol and data transfer can be according to any know standard (such as ASTM or HL7).

A method for managing analytical tests is provided. The method can include storing a first set of instructions in a memory of an analyzer configured to perform an analytical test on a biological sample, storing a second set of instructions in a memory of a test manager module, and receiving a test order for one of an analytical test of a first type and an analytical test of a second type in the test manager module through a first test order interface. The method can further include determining in the test manager module if the test order is for the analytical test of the first type or the analytical test of the second type, and if the test request is determined to be for the analytical test of the first type, forwarding the test order directly to the analyzer to analyze the biological sample according to the first set of instructions, and if the test order is determined to be for the analytical test of the second type, generating in the test manager module, according to the second set of instructions, one or more secondary test requests, and transmitting the one or more secondary test requests to the analyzer.

In another embodiment, the method can further include storing in the analyzer memory, a first set of instructions of a first type and a first set of instructions of a second type, and analyzing the biological sample according to the first set of instruction of the first type if the test order is for the analytical test is of the first type, and analyzing the biological sample according to the first set of instructions of the second type in response to the one or more secondary test requests if the test order is for the analytical test is of the second type. For example, the first set of instructions of the first type can be used by the analyzer to process an order for a single analytical result and the first set instructions of the second type can be used by the analyzer to perform a test controlled by the test manager module according to the second set of instructions.

Figure 3:
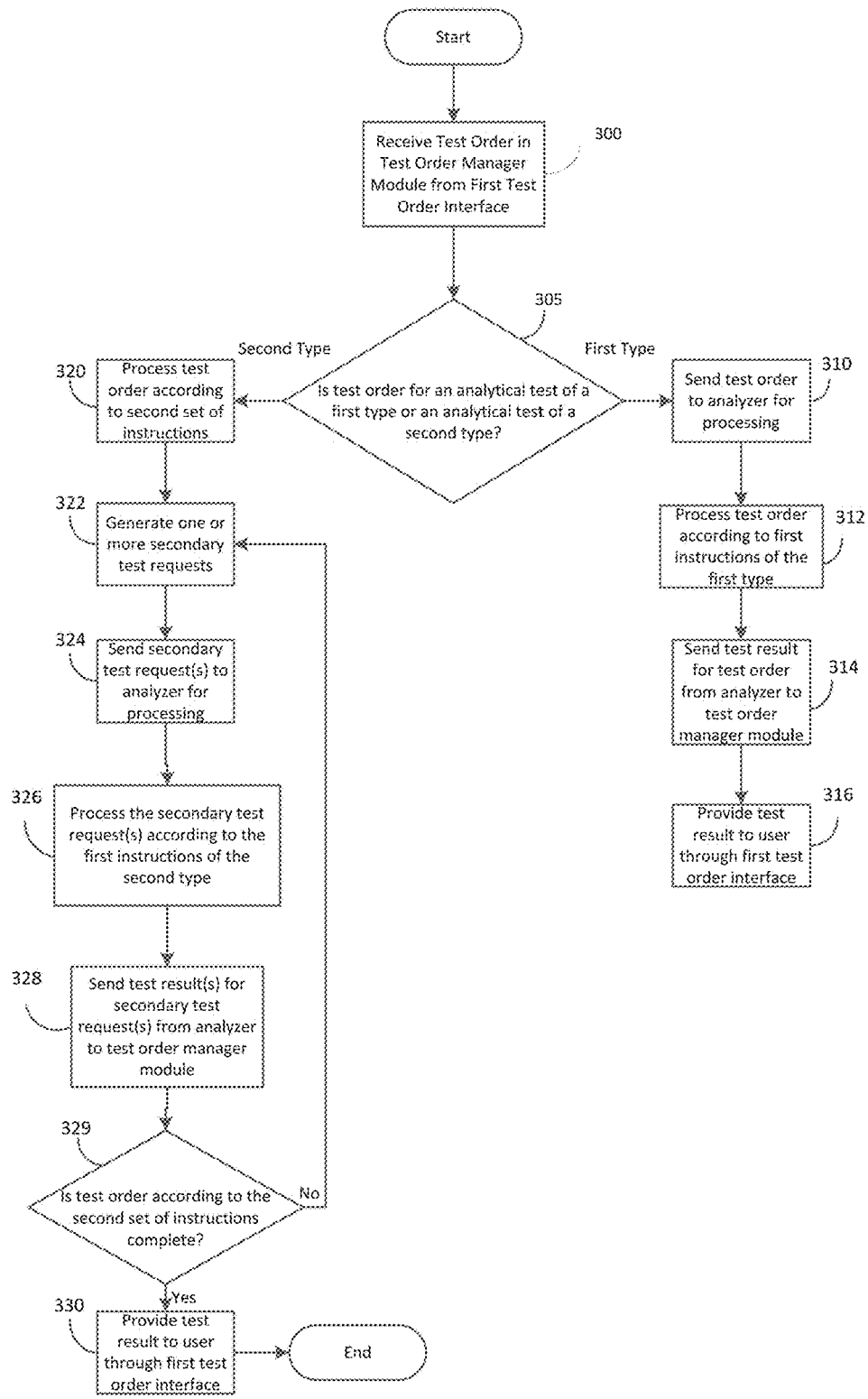
FIG. 3 illustrates method for analytical test management according to an embodiment of the present disclosure.

One embodiment of the logic of the disclosed method is shown in FIG. 3. At 300, a test order can be received at the test order management module from the first test order interface. Upon receipt, a determination as to whether the test order is for an analytical test of the first type or the test order is for an analytical test of the second type. If the test order is for an analytical test of the first type, the test order can be directly sent to an analyzer for processing 310, and if the test order is for an analytical test of the second type, the test order can then be processed by the test order manager module according to the second set of instructions.

Following the right hand side of FIG. 3, a test order for an analytical test order of the first type, once sent to an analyzer 310, can be processed by the analyzer according to first instructions of the first type 312 to provide a test result for the analytical test of the first type, which test result can be sent to the test order manager module 314. The test order manager module can then provide the test result for the analytical test of the first type available to a user through the first test order interface 316.

Also as shown in left hand side of FIG. 3, the test order manager module can process the test order for an analytical test of the second type 320 and generate one or more secondary test requests 322. The one or more secondary test requests can then be sent to an analyzer for processing 324. The analyzer to which the test order manager module sends the one or more secondary test requests can be the same or different from the analyzer to which a test order for an analytical test of the first type is sent. For example, in some embodiments, one analyzer can be configured to process only test orders for analytical tests of the first type and another analyzer can be configured to process test orders for both an analytical test of the first type and for an analytical test of the second type. In such an embodiment, linking of reagents for use in processing of analytical tests of the second type can be performed only in one analyzer and any waste of reagents that can occur because linked reagents are made unusable together can be avoided.

As shown also on the left hand side of the embodiment of FIG. 3, the one or more secondary test requests generated at 322 can be sent to the analyzer 324 and can be processed by the analyzer according to first instructions of the second type 326. A test result (or results) of processing the one or more secondary test requests can be sent from the analyzer to the test order manager module 328, once received at the test order manager module, the test result (or results) of processing the one or more secondary test results can be further processed by the test order manager module according to the second set of instructions, and if the processing according to the second set of instructions is complete a test result can be provided to a user through the first test order interface 330 and the test order for the analytical test of the second type can be fulfilled. For example, a first one or more secondary test requests may provide a test result that according to the second set of instructions can indicate no further testing is necessary as the answer is already provided. An advantage to having such a gating test can be that further tests according to further secondary test requests may not be needed, and resources can be conserved automatically.

On the other hand, as shown in the left side of the embodiment of FIG. 3, if the first one or more secondary test requests can yield a test result or results that when further analyzed by the test order manager module can be determined by the test order manger module according to the second set of instructions to require further testing, the test order manager module can generate a second one or more secondary test requests 322 and the process can be repeated, one or more additional times, such as with third, fourth, fifth or even more additional secondary test requests being generated by the test order manager module until a determination can be made at 329 that the test order according to the second set of instructions is complete and a final test result can be provided at 330. An advantage of having such an automated sequence can be that complex decision trees can be taken out of the hands of inexperienced health care providers and can be used to produce reliable results. Furthermore, since in some embodiments, a biological sample can be kept on an analyzer until a final result is provided, regardless of how many secondary test requests may be needed to provide a reliable final result, time may not be wasted storing a sample and retrieving it multiple times and expiration of the time during which valid test results can be obtained from the sample can be avoided, and thus, the need to take additional samples from a patient can be avoided. Avoidance of sample waste can be especially important when the sample can be scarce, such as a blood sample from a tiny, premature infant.

In even more embodiments, the first instructions of the first type and the first instructions of the second type can lead to the same set of analytical steps being performed by the analyzer, but in the case of the first instructions of the second type, those instructions can be linked to one or more additional first instructions of the second type through the second set of instructions used by the test manager module directs the analyzer in performing analytical tests of the second type. Linking of additional tests through the second set of instructions can be controlled either by the analyzer querying the test manager to determine which tests can be linked, or through the presence in the analyzer memory of first instructions of the second type.

In still more embodiments, the linking of tests through the second set of instructions can also lead to linking of reagents used by the analyzer so that the resources necessary to carry out a particular analytical test of the second type can be reserved for use in that particular test. For example, the analytical test of the second type can be a complex combination of individual tests that together can be used to calculate a final test result and perhaps an associated quality control measure and it can be desirable to ensure that all reagents needed to perform the test are available.

Figure 4A:
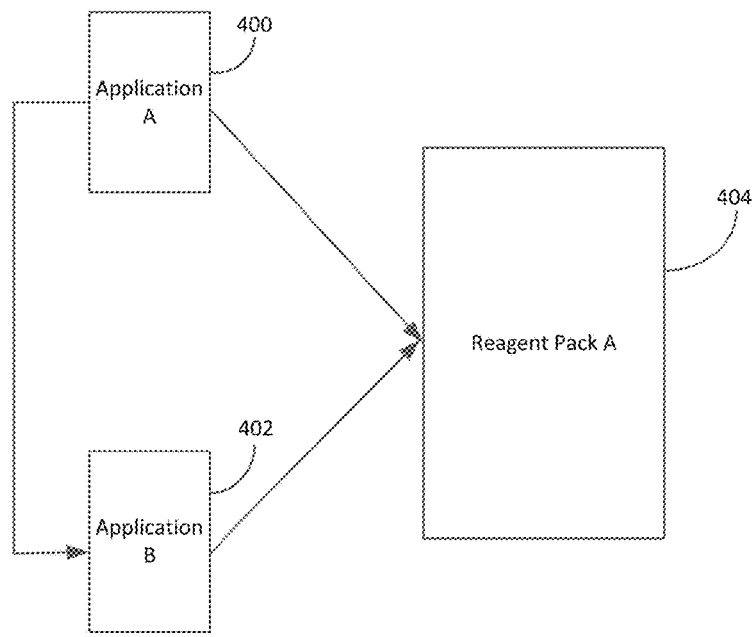
FIGS. 4A-B illustrate embodiments of linked test applications/reagents and logically linked test applications/reagents according to the present disclosure.
Figure 4B:
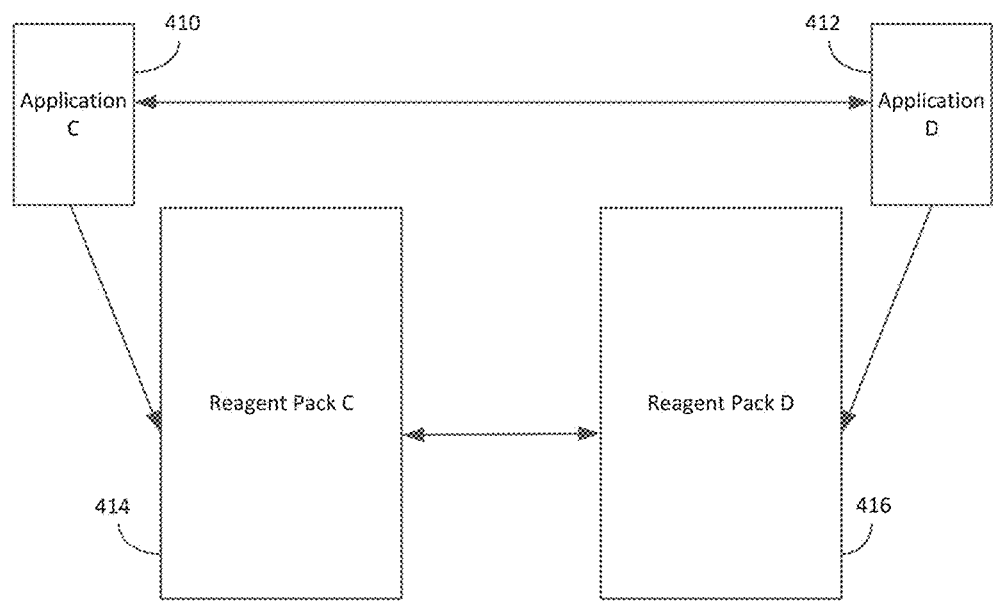

Example 1: Linking of Reagents for Analytical Tests of the Second Type Under Control of the Test Manager Module The pipetting sequence of some assays can influence the reliability of certain tests. For those assays, it can be that no other pipetting of additional reagents can be done in between the use of two or more particular reagents, and it can be desirable that pipetting steps should be as close to each other in time to produce best analytical performance. As shown in FIGS. 4A-B, reagents can be linked within one reagent pack (which itself could include one or more reagents) or between two or more reagent packs (which can also include one or more reagents each).

Once linked, pipetting sequences can be defined on an analyzer, and individual applications of linked tests can then be pipetted in a first predetermined sequence for a particular biological sample. In certain embodiments, in case of a measurement failure of at least one of the linked tests, all individual tests can be repeated again in a second predetermined order, which can be the same or different from the first predetermined order.

In the embodiment of FIG. 4A, two first sets of instructions of the second type 400, 402 can be linked through their used in an analytical test of the second type and can be used in response to one or more secondary test requests generated in the test manager module. The linkage, in this case between the two first sets of instructions of the second type 400, 402 and the reagent pack 404, can be a logical link (also referred to linked tests) because both first sets of instructions of the second type utilize the same reagent pack 404 during execution of the secondary test requests. In some embodiments, the link between multiple applications of the same reagent pack 404 can be established through an application parameter that can be associated with linked first sets of instructions of the second type, and according to this parameter as recognized by the analyzer CPU, linkage of the reagent between tests can be established during loading of the reagent pack (so as, for example, to ensure that enough reagent for all applications that use the reagent can be maintained). In some embodiments, a logical link can be implemented in a one way direction where as one of the application can be the master application and all additional linked applications then can be refer to the master application. Thus, there can be a Master/Slave relationship between two or more first sets of instructions of the second type, and one of them, such as 400, can be used also to process a test request for an analytical test of the first type. Also, in some instances, a QC determination for one set of instructions 400 can be copied and used for the other set of instructions 402.

Alternatively, as show in the embodiment of FIG. 4B, two or more reagent packs that are used together in response to two or more secondary test requests can be provided in one kit with one kit lot number. In this instance, there can be no Master/Slave relationship between the sets of first instructions of the second type 410, 412 since in some embodiments, the sets of first instructions of the second type can always be together for each test order (or possibly repeat). Not only are the sets of first instructions of the second type 410, 412 linked, but also the reagent packs 414, 416 as shown. Such a linkage between sets of first instructions of the second type and two or more different reagent packs can be referred to as linked kits.

Also in the embodiment of FIG. 4B, the first sets of instructions of the second type linked as a kit can also be linked through an application parameter present in the instructions, which can be used by the analyzer CPU to link the reagent packs 414, 416 and the linkage of the reagent packs can be done on system during loading. And, again, it is possible, once the reagent packs are linked, to pipette from the linked reagent packs in a first predetermined sequence for a biological sample, and, in case of a measurement failure and repeat, the reagents can be again pipetted in a second predetermined sequence that can be the same as or different from the first predetermined sequence.

It can be possible, in some embodiments, to have both linked tests (using the same reagent pack) and linked kits (of two or more reagent packs) employed in executing a test order for an analytical test of the second type according to one or more secondary test requests generated in the test order manager module.

Linkage of reagent during loading can have the advantage compared to a possible linkage during production of the reagent packs. If the reagent packs would be linked during production, the whole production process and also the user when unpacking may have to take care to ensure that the linked reagent packs are loaded together as a package to the analyzer. With linkage during the loading process, the analyzer can combine any reagent packs from the same lot into a combination of multiple reagent packs. In certain embodiments, reagent packs, once linked, cannot be loaded or unloaded from an analyzer separately.

Furthermore, in some embodiments, based on linkage information, the analyzer can schedule and processes the pipetting sequences as required. In these embodiments, secondary test requests sent form the test order manager module based on the second set of instructions may not have to include information specific instructions regarding pipetting sequences, thereby potentially simplifying development of new tests by a vendor.

Example 2: Restricted Pipetting Order for Linked Reagents

Linkage (logical or as kits) according to the embodiments of FIGS. 4A-B above can allow definition of predetermined pipetting orders for reagents. In this example, two specific types of defined pipetting sequences can be presented for linkage as kits, which pipetting sequences differ in the way that repeat tests can be handled in case of failure of a test according to a secondary test request.

Figure 5:
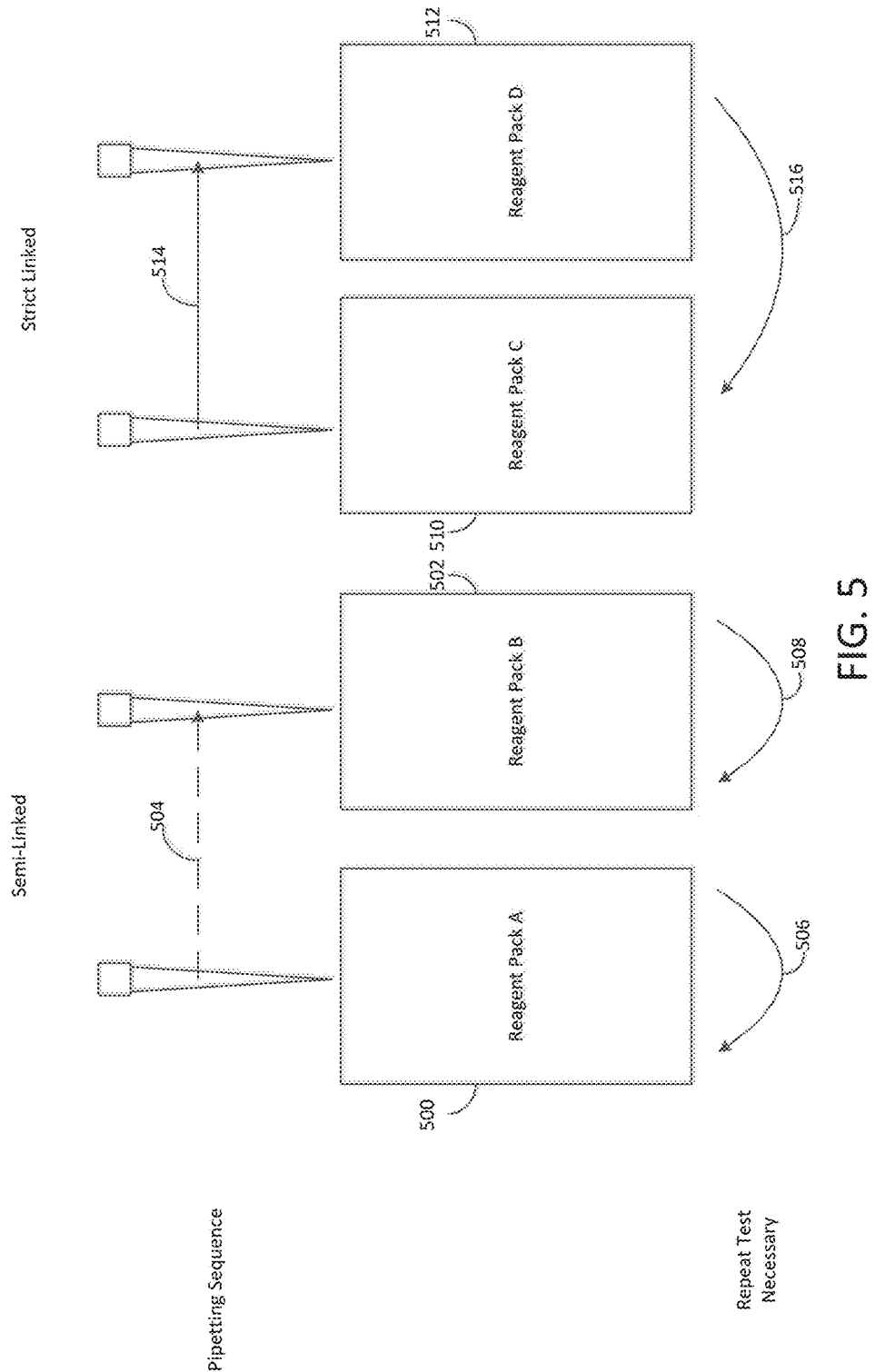
FIG. 5 illustrates how repeat pipetting can controlled within linked tests according to an embodiment of the present disclosure.

In the scheme of FIG. 5, shown with reagent packs A and B 500, 502, referred to as semi-linked, the pipetting order for the test can be defined as proceeding from pack A to pack B 504. When either one or both of the two tests fail, only the test that failed may need to be repeated, either a repeat of the test using reagent pack A 506 or reagent pack B 508. In the scheme of FIG. 5, shown with reagent packs C and D 510, 512, referred to as strict linked, the pipetting order can be defined as proceeding from pack C to pack D 514. When either one or both of the two tests fail, both the test using reagent pack C 510 and the test using reagent pack D 512 can be repeated according to the same order 514. An advantage of strict linking can be that it can ensure that when the testing order using multiple reagents is important, it can be easily implemented in a second set of instructions.

Example 3: Representative Analytical Tests of the Second Type

In this example, representative analytical tests that can be carried out under the control of the disclosed test order manager module are described. As used in this example and in the accompanying FIGS. 6, 7 and 8, "ACN" can refer to a set of instructions, which if present in the test manager module can represent a second set of instructions and, if present in the analyzer, can represent either a first set of instructions of the first type ("direct use") or a first set of instructions of the second type ("restricted").

Figure 6:
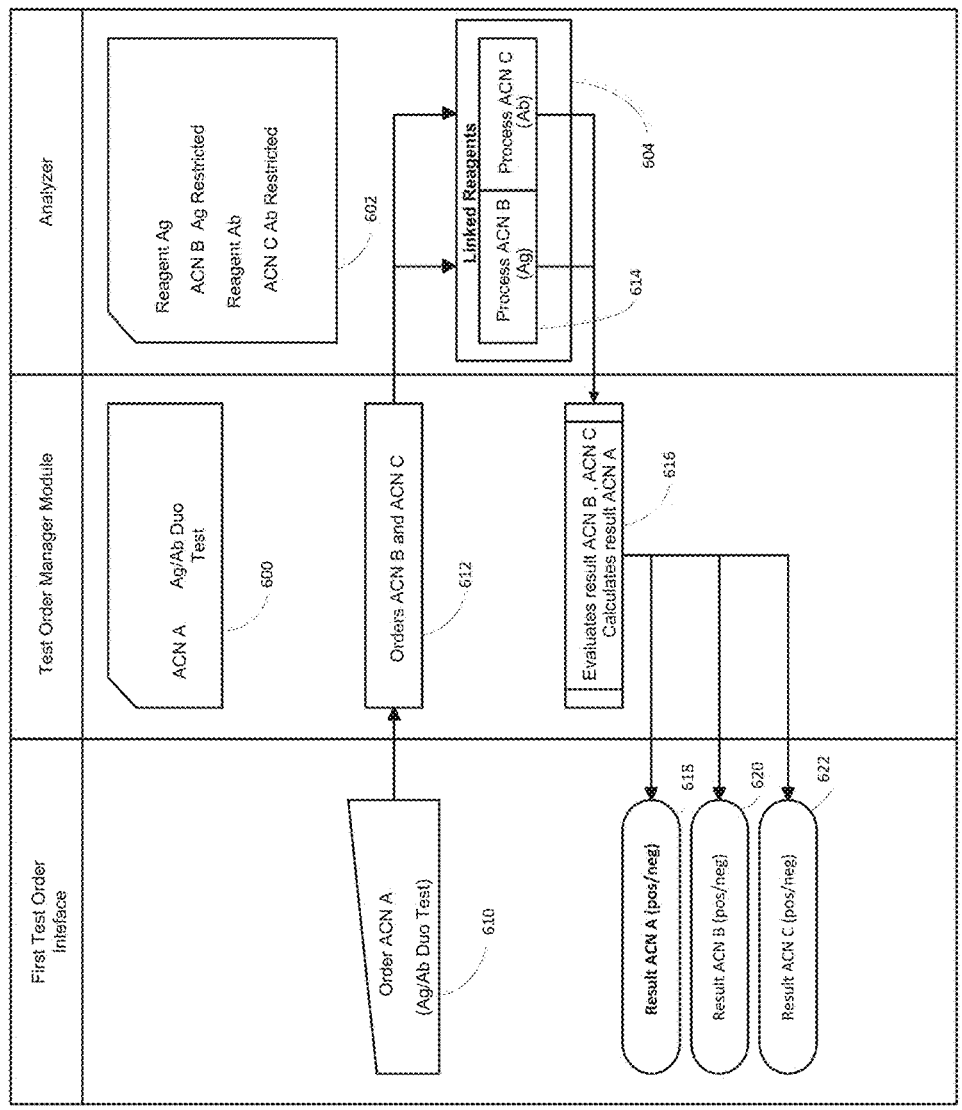
FIG. 6 illustrates an analytical test of a second type according to an embodiment of the present disclosure.

FIG. 6 shows the interplay between the first test order interface, the test order manager module, and the analyzer in carrying out an antigen (Ag)/antibody (Ab)dual test (e.g. for HCV, HBV, HIV, Chikungunya, EBV, or the like). In this example, the test order manager module is shown as having stored in its memory an ACN A 600 for an Ag/Ab dual test. The analyzer is shown having loaded a reagent for the Ag test and a reagent for the Ab test, and stored in its memory an ACN B for a restricted Ag test and an ACN C for a restricted Ab test 602. Upon receipt of a test order 610 for the Ag/Ab dual test from the first test order interface, the test order manager module can determine that the test order is for an analytical test of the second type and can begin processing the test order 610 according to ACN A 600, to generate secondary test requests for ACN B and ACN C 612, which can be transmitted to the analyzer, which can process these ACNs in parallel using the linked reagents 604 (linked kits) and can send the results back to the test order manage module 614. The results of the secondary test requests can be then evaluated (such as for quality, in range, out of range, etc.), and if, for example, the results are deemed reliable, a test result for ACN A can be calculated in the test order manager module 616, according to ACN A, and one or more results can be provided to the first test order interface 618, 620, 622 at the end of the process. The one or more results can then be provided to a user interface for display. In some embodiments, only the result of ACN A can be displayed, and in other embodiments the result for ACN B and/or ACN C can also be displayed or can be displayed as a drill-down when the result for ACN A can be selected on the display.

Figure 7:
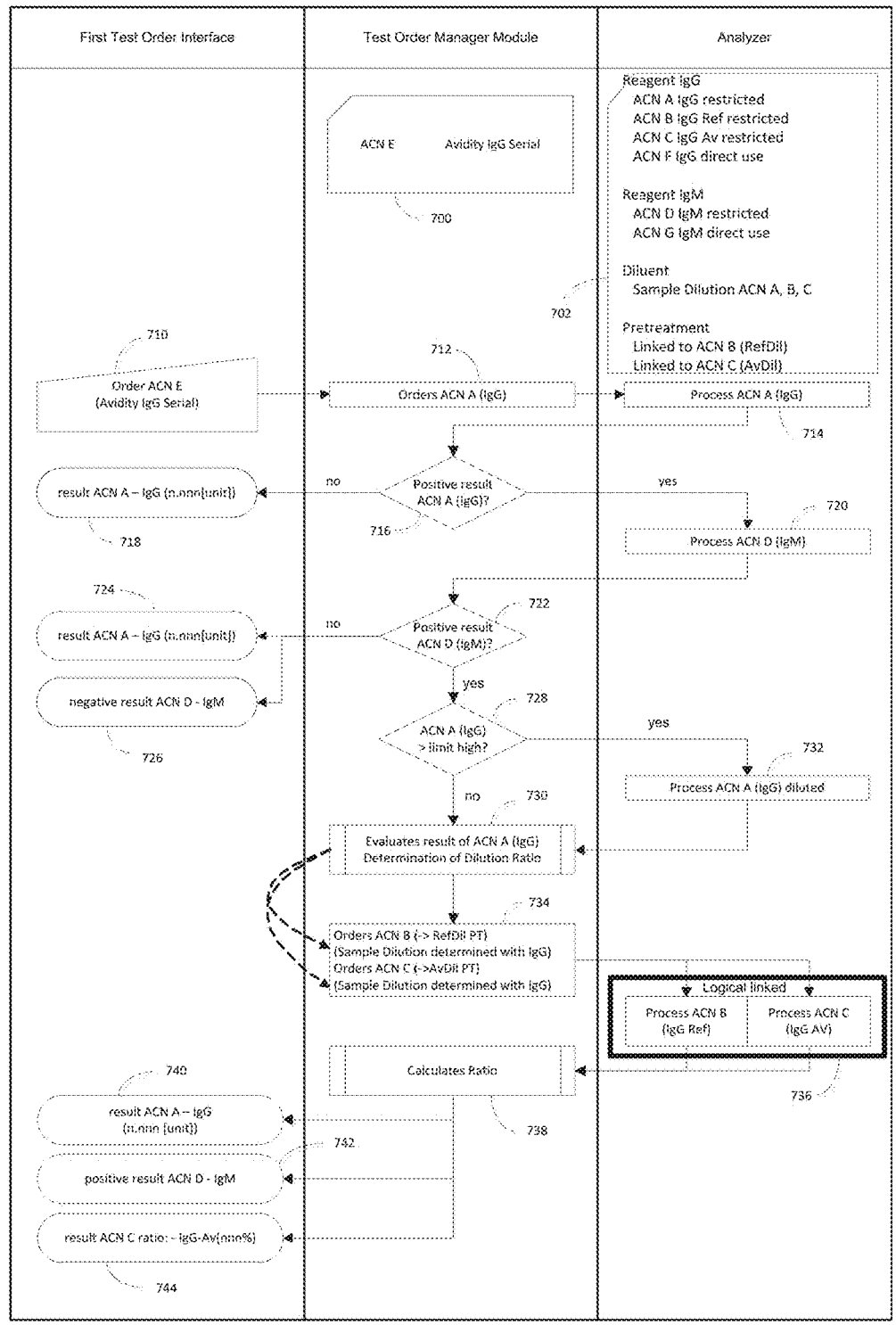
FIG. 7 illustrates an analytical test of a second type according to another embodiment of the present disclosure.

FIG. 7 shows the interplay between the first test order interface, the test order manager module, and the analyzer in carrying out a complex serological testing scheme (e.g. the Avidity IgG Serial scheme shown) that can include several decision points made according to the second set of instructions stored in the memory of a test manager module and that can also illustrate the logical linking of tests. In this example, the test order manager module is shown as having stored in its memory an ACN E 700 for an Avidity IgG Serial test. The analyzer is shown having loaded a reagent for the an IgG test, a reagent for an IgM test, a Diluent, and a Pretreatment reagent, and stored in its memory an ACN A for a restricted IgG test, an ACN B for a restricted IgG reference test, an ACN C for a restricted IgG Avidity test, an ACN F for a direct use IgG test (as an example of first set of instructions of a first type for performing an analytical test of the first type, which would be used upon forwarding of a test order for ACN F directly from the test order manager module to the analyzer), an ACN D for a restricted IgM test, and an ACN G for a direct use IgM test 702.

With further reference to FIG. 7, when an order for ACN E is received at the first test order interface 710 and forwarded to the test order manager module, the test order manager module can recognize the test order as an order for an analytical test of the second type and can begin processing the order according to ACN E to generate a secondary test request for ACN A 712 that is then transmitted to the analyzer, which can process ACN A 714 and send the result of the test back to the test order manager module, where, according to ACN E, it can be determined whether the test result for ACN A was positive or negative 716. If the test was negative (no), the result can be provided to the first test order interface 718 and the sequence can be terminated. If the test was positive (yes), the test order manager module can generate an additional secondary test request for ACN D and transmit that to the analyzer, which can process the test request according to ACN D 720. The result of ACN D can be transmitted back to the test order manager module where, according to ACN E, it can be determined whether the result of ACN D was positive 722. If the result was negative (no), the test order manager module can send a result for ACN A and a negative result for ACN D to the first test order interface, and the process can end. If the result was positive, the test order manager module, according to ACN E, can determine if the result of ACN A was above a certain predetermined threshold 728. If yes, then the test order manager module can generate a further secondary test request for an additional test according to ACN A with dilution, which can be transmitted to and processed by the analyzer to provide a test result that can be sent back to the test order manager module 732. The test manager module can then evaluate either the original test result for ACN A or the diluted result for ACN A to determine a dilution ratio 730. In either case, the test order manager module can then generate secondary test requests for the logically linked ACN B and ACN C tests 734, which can be transmitted to the analyzer for processing to provide results back to the test order manager module 736. The test results can then be used according to ACN E to calculate a ratio 738, and the process can end when the test order manager module transmits to the first test order interface a result for ACN A 740, a positive result for ACN D 742, and the ratio result for ACN C 744. Any of or all of the various results provided to the first test order interface by the test manager module can then be transmitted to and displayed, either in a primary display, or in a drill-down display, on a user interface.

Figure 8:
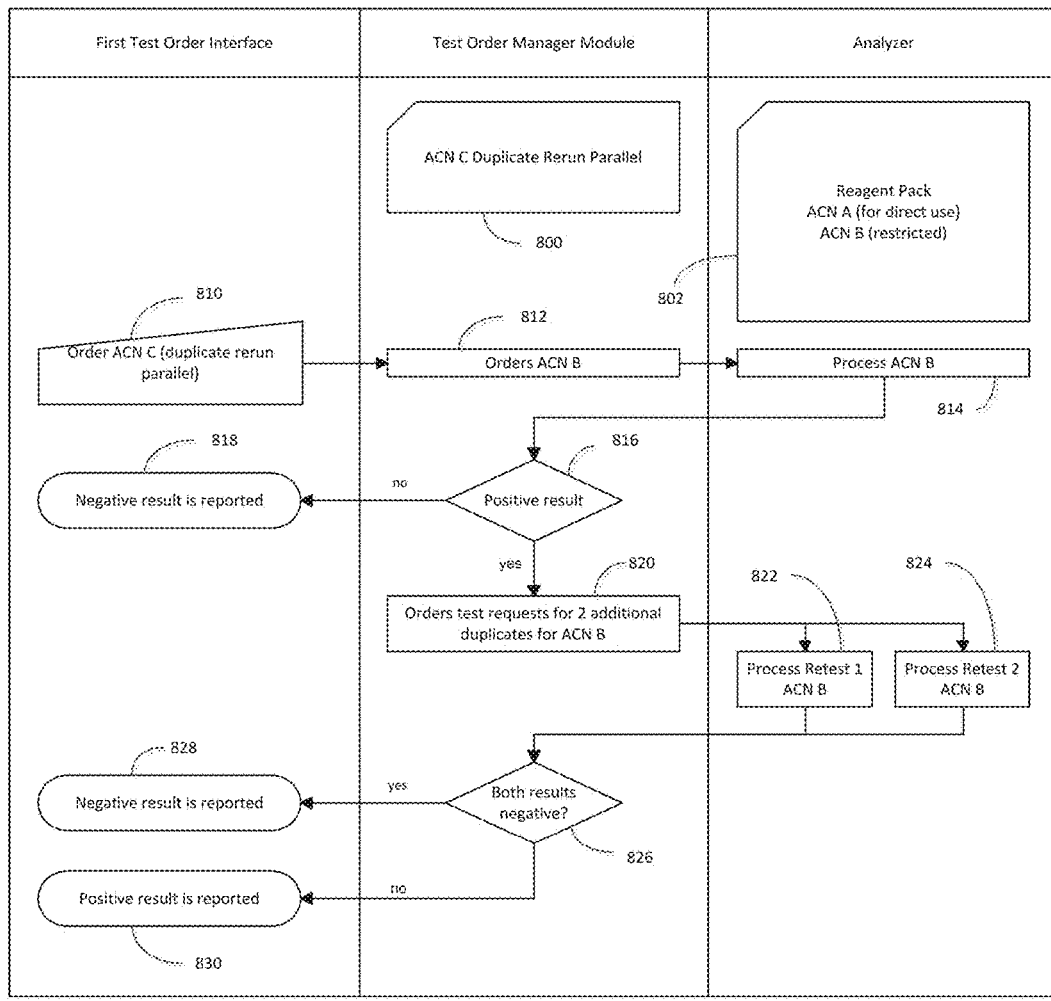
FIG. 8 illustrates an analytical test of a second type according to yet another embodiment of the present disclosure.

FIG. 8 shows the interplay between the first test order interface, the test order manager module, and the analyzer in carrying out an automated duplicate testing scheme. In this example, the test order manager module is shown as having stored in its memory an ACN C 800 for a parallel duplicate rerun testing scheme. The analyzer is shown having loaded a single reagent pack and an ACN A for direct use and a restricted ACN B 802. When a test order for ACN C arrives at the first test order interface 810 and is transmitted to the test order manager module, the test order manger module can recognize the test order as being for an analytical test of the second type and can generate a first secondary test request for ACN B 812, which can then be transmitted to the analyzer for processing and generation of a first result for ACN B 814. Upon receiving the first result for ACN B from the analyzer, the test order manager module can determine if the first result for ACN B is negative (no) or positive (yes) 816. If the result of the first result for ACN B is negative, the result can be transmitted to the first test order interface and the process of ACN C can end 818. If the first result for ACN B is positive (yes), the test order manager module can generate second and third secondary test requests for ACN B 820 and can transmit them to the analyzer for processing and transmission back to the test order manager module 822, 824. The test manager module can then determine whether the results for both the second and third secondary test requests for ACN B are negative 826, and if they both are negative (yes), a negative result can be transmitted to the first test order interface and the process according to ACN C can stop 828. If both results are not negative (no), a positive result can be transmitted to the first test order interface and the process according to ACN C can stop 830.

Due to the flexibility provided by carrying out testing using a test order manager module, it can be possible to combine aspects of the different processes illustrated in FIGS. 6, 7 and 8, and to perform other variations thereof. For example, instead of parallel retesting in duplicate as shown in FIG. 8, retesting can be ordered serially until a minimum number of like results can be obtained. Or, for example, a positive result for the process of FIG. 6 can initiate parallel retesting of the entire sequence of FIG. 6 in duplicate according to the scheme of FIG. 8. In this manner, an impactful diagnosis (such as HIV positive) can be automatically repeated two or more times to help ensure that a misdiagnosis may not be provided to a patient and thus spare the patient unnecessary anguish.

Example 4: Calculated QC

In addition to handling the automated ordering of secondary test requests and performing calculations to provide a test result, the test order manager module can perform quality control (QC) calculations based upon QC measurements where the ordered test itself does not lend itself to direct QC measurement. For example, where two different linked tests are used to provide test results that are used to calculate a final result, the QC measure for the final result cannot be based on a QC measurement for a single test on which the final result is based. Furthermore, when a final result is based upon a combination of measurements that are either obtained using multiple, different measuring modules (perhaps in the same or different analyzers, and perhaps of the same or different types), it can be important to provide a quality control measure that can reflect the performance of the measuring modules that were used to make the measurements on the biological sample.

Figure 9:
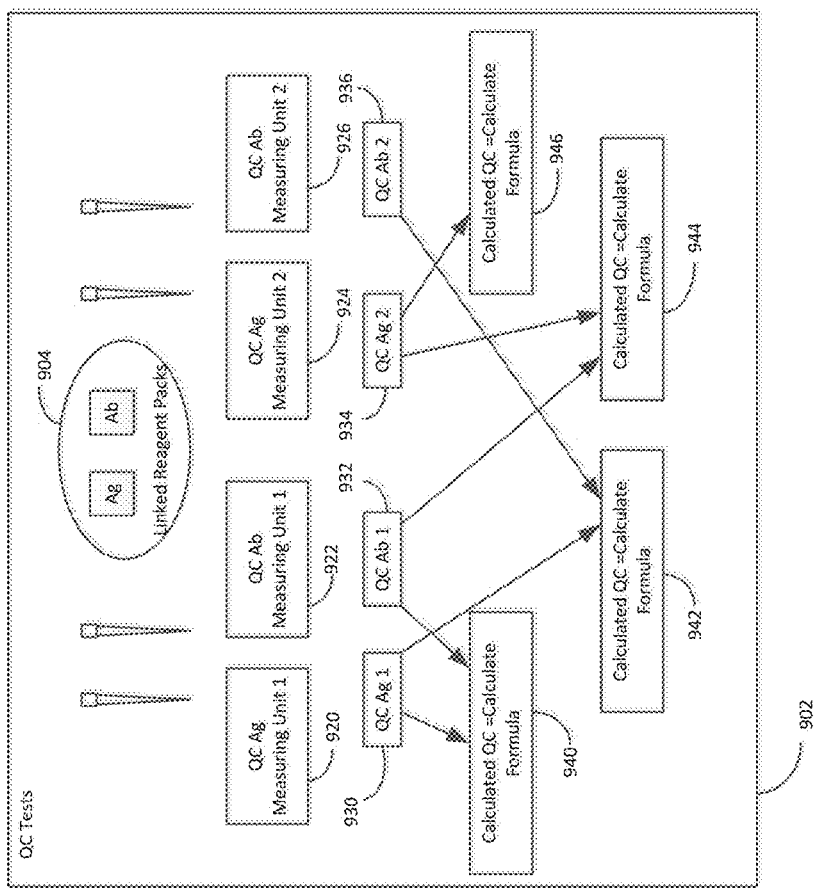
FIG. 9 illustrates an embodiment for calculated QC in the case of multiple measuring units according to the present disclosure.
Figure 9:
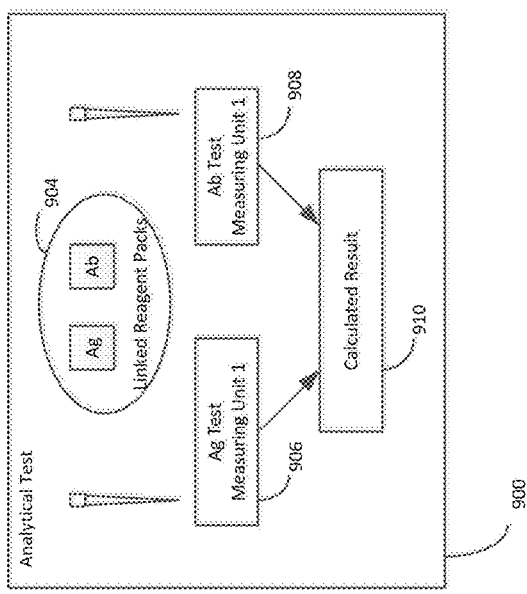

FIG. 9 illustrates an embodiment showing how a calculated QC can be provided for a test like that shown in FIG. 6, where the analyzer can include two different measuring cells. In this embodiment, the analytical test 900 can involve the use of linked reagent packs 904, one for the Ag test and one for the Ab test that are used, for example, one after the other in the same measuring unit (measuring unit 1) to generate test results for the Ag and Ab 906, 908, respectively. These results can be transmitted to and used by the test manager module to provide a calculated test result 910. Meanwhile, in parallel, QC measurements can be made periodically or in a triggered fashion for both the Ag test and Ab test in both of the measuring units of the analyzer 902, using the same set of linked reagent packs 904 that can be used to provide the calculated test result 910. QC results 930, 932, 934, and 936, respectively can thus be obtained for Ag in measuring unit 1 920, Ab in measuring unit 1 922, Ag in measuring unit 2 924, and Ab in measuring unit 2 926. The various QC results can then be used to provide four different calculated QC measures 940, 942, 944 and 946 that can correspond to each of the combinations of how two test results can be generated in two different measuring units. The appropriate calculated QC 940 can then be assigned to the calculated result 910, which in this case can mean the calculated result obtained with sequential measurement of Ag and Ab in measuring unit 1 can be assigned the QC result calculated from a QC measurement for Ag in measuring unit 1 and a QC measurement for Ab in measuring unit 1.

An advantage to a calculated QC scheme such as the one illustrated in FIG. 9 can be that it can provide the possibility to create a QC result for a test result based on multiple test measurements, which can be a regulatory requirement. Furthermore, an additional advantage can be that anytime a new multi-test assay is developed, the test order manager module can be configured to provide a corresponding calculated QC measure, and such calculated QC measure schemes can be installed in parallel with, and possible as part of, a second set of instructions. Thus, whenever QC results are measured on the analyzer, a calculated QC can be provided for linked tests. And, if there are multiple measuring units, QC measurement for each test can be done on each measuring cell. If, for example, a formula for a calculated QC can contain multiple QC measures, all combinations of QC measures and measuring units can be produced. In order to avoid useless calculations of QC results, it can be desirable, but not necessary that all the QC measures be produced in the same run, which can mean pipetting for the QC measures can be used to generate a calculated QC measure need only be in a timely related sequence, meaning from the same QC order, and not necessarily in a predetermined order.

In one embodiment, all combinations of calculated QC results out of on QC run can be pre-calculated and can be assigned to a calculated sample result. After a sample is measured, the correct calculated QC result can thus be assigned to the sample result. In other embodiments, such as where one measuring unit can be reserved for performing analytical tests of the second type that utilize calculated QC, only QC measures for that particular unit may need to be combined to provide calculated QC measures.

Although described above primarily with respect to combinations of tests being performed on a particular analyzer according to the second set of instructions that are used to generate secondary test requests that can be used directly or to generate additional secondary test requests on a conditional basis, the system and method described herein can be applied to even more complex combinations of tests used to reach a diagnostic result. Such more complex combinations can involve multiple analyzers, perhaps of multiple different types, analyzing one or more biological samples from a single patient (or for epidemiological purposes, multiple patients), and also perhaps multiple different types of biological samples. For example, in the area of hematology, it can be advantageous to combine results from two or more of, in any combination, a cell counting analyzer (CBC/Differential), a cellular morphology analyzer (microscopic analysis), a red blood cell sedimentation rate analyzer (physical analysis), a flow cytometer for measuring CD markers (immunological analysis), a clinical chemistry analyzer configured to perform an HbA1c test (chemical analysis), a platelet function analyzer (can be an electro-physical analyzer), a blood gas analyzer (can be an electrochemical analyzer) and a nucleic acid analyzer to reach a desired diagnosis quickly and reliably. In such embodiments, the test manager module of the disclosed system can be configured according to the second set of instructions to not only exchange test orders and test results through the first test order interface with a middleware and/or host system, but can also send a request through the interface to an LIS or HIS for an additional patient sample. In one embodiment, a health care provider can be alerted by the disclosed system to obtain the needed sample and instructed to forward the sample to the laboratory.

Furthermore, while described as a separate computer system a computer system controlling an analyzer, it can also be possible for the test order manager module to be a component of a computer system controlling one or more analyzers. In such embodiments, it can still be possible to maintain vendor control over the identity and content of the second sets of instructions stored in a test manager module memory.

It is noted that terms like "preferably," "commonly," and "typically" are not utilized herein to limit the scope of the claimed embodiments or to imply that certain features are critical, essential, or even important to the structure or function of the claimed embodiments. Rather, these terms are merely intended to highlight alternative or additional features that may or may not be utilized in a particular embodiment of the present disclosure.

Having described the present disclosure in detail and by reference to specific embodiments thereof, it will be apparent that modifications and variations are possible without departing from the scope of the disclosure defined in the appended claims. More specifically, although some aspects of the present disclosure are identified herein as preferred or particularly advantageous, it is contemplated that the present disclosure is not necessarily limited to these preferred aspects of the disclosure.

We claim:

1. An analytical test management system, the analytical test management system comprising:
   an analyzer configured to perform an analytical test on a biological sample according to a first set of instructions, the first set of instructions stored in an analyzer memory;
   a test manager module communicatively connected to the analyzer, the test manager module configured to direct activity of the analyzer according to a second set of instructions, the second set of instructions stored in a test manager module memory;
   a first test order interface communicatively connected to the test manager module, the first test order interface configured to receive a test order for one of an analytical test of a first type and an analytical test of a second type and to transmit the test order to the test manager module, wherein if the test order is for the analytical test of the first type, the test manager module is configured to forward the test order directly to the analyzer and the biological sample is analyzed by the analyzer according to the first set of instructions and wherein if the test order is for the analytical test of the second type, the test manager module is configured to handle the test order according to the second set of instructions and to generate and transmit one or more secondary test requests to the analyzer.

2. The system according to claim 1, wherein the analyzer memory comprises a first set of instructions of a first type and a first set of instructions of a second type, wherein the first set of instructions of the first type is used by the analyzer to process the test order for the analytical test of the first type and the first set of instructions of the second type is used by the analyzer to process the test order for the analytical test of the second type according to the one or more secondary test requests.

3. The system according to claim 2, wherein the first set of instructions of the first type can be initiated through either the first test order interface or a second test order interface, the second test order interface communicatively connected directly to the analyzer and bypassing the test manager module, and wherein the first set of instructions of the second type can only be initiated through the first test order interface.

4. The system according to claim 2, wherein the analyzer comprises an analyzer processor configured to, upon loading of a first reagent into the analyzer, determine whether the first reagent is to be used for the analytical test of the first type according to the first set of instructions of the first type or is to be used for the analytical test of the second type according to the first set of instructions of the second type, and if the first reagent is to be used for the analytical test of the second type according to the first set of instructions of the second type, the analyzer processor is configured to link the first reagent to a second reagent used for the analytical test of the second type.

5. The system according to claim 4, wherein the analyzer processor is configured to determine if either of the first reagent or the second reagent is no longer usable, and if either the first reagent or the second reagent is determined no longer usable, the other of the first reagent and the second reagent is also made unusable by the analyzer processor.

6. The system according to claim 4, wherein the first reagent and the second reagent are utilized according to the second set of instructions in a predetermined order.

7. The system according to claim 6, wherein if an analytical test result obtained using either one of the first reagent and the second reagent is in error, a repeat analytical test is automatically ordered by the test manager module and the first reagent and the second reagent are both again utilized according to the second set of instructions in the predetermined order to generate a repeat analytical test result.

8. The system according to claim 2, wherein the first set of instructions of the first type and the first set of instructions of the second type are identical except that the first set of instructions of the first type are used only for performing the analytical test of the first type whereas the first set of instructions of the second type are used only for performing the analytical test of the second type as directed by the test manager module according to the second set of instructions.

9. The system according to claim 8, wherein a quality control result obtained by the analyzer according to the first set of instructions of the first type is transmitted to and used by the test manager module as a quality control result for an analytical result of an analytical test on the biological sample according to the first set of instructions of the second type.

10. The system according to claim 1, wherein the one or more secondary test requests generated by the test manager module and transmitted to the analyzer comprise at least two secondary test requests, wherein the at least two secondary test requests are used by the test manager module to determine an analytical result for the analytical test of the second type.

11. The system according to claim 1, wherein the one or more secondary test requests generated by the test manager module and transmitted to the analyzer comprise at least a first secondary test request that is used by the analyzer to generate a first secondary test result that is transmitted back to the test manager module.

12. The system according to claim 11, wherein the test manager module is configured according to the second set of instructions to determine based on the first secondary test result whether one or more additional secondary test requests are required, and if the one or more additional secondary test requests are required, to generate and transmit the one or more additional secondary test requests to the analyzer.

13. The system according to claim 1, further comprises, a graphical user interface, the graphical user interface configured to display to a user a final result, the final result determined based on one or more secondary test results received from the analyzer following execution of the one or more secondary test requests by the analyzer, wherein the one or more secondary test results used to determine the final result are hidden from the user.

14. A method for managing analytical tests, the method comprising:
storing a first set of instructions in a memory of an analyzer configured to perform an analytical test on a biological sample;
storing a second set of instructions in a memory of a test manager module;
receiving a test order for one of an analytical test of a first type and an analytical test of a second type in the test manager module through a first test order interface;
determining in the test manager module if the test order is for the analytical test of the first type or the analytical test of the second type;
if the test request is determined to be for the analytical test of the first type, forwarding the test order directly to the analyzer to analyze the biological sample according to the first set of instructions; and
if the test order is determined to be for the analytical test of the second type, generating in the test manager module, according to the second set of instructions, one or more secondary test requests, and transmitting the one or more secondary test requests to the analyzer.

15. The method according to claim 14, further comprises,
storing in the memory of the analyzer a first set of instructions of a first type and a first set of instructions of a second type.

16. The method according to claim 15, further comprises,
analyzing the biological sample according to the first set of instruction of the first type if the test order is for the analytical test is of the first type; and,
analyzing the biological sample in response to the one or more secondary test requests according to the first set of instructions of the second type if the test order is for the analytical test is of the second type.

* * * * *